(12) United States Patent
Milner et al.

(10) Patent No.: US 8,067,572 B2
(45) Date of Patent: Nov. 29, 2011

(54) HYBRID INTERFERING RNA

(75) Inventors: Josephine Anne Milner, Heslington (GB); Michael Gait, Cambridge (GB); Ming Jiang, Heslington (GB); Andrei Arzumanov, Cambridge (GB)

(73) Assignee: The University of York, Heslington, York (GB)

( * ) Notice: Subject to any disclaimer, the term of this patent is extended or adjusted under 35 U.S.C. 154(b) by 0 days.

(21) Appl. No.: 11/915,147

(22) PCT Filed: May 24, 2006

(86) PCT No.: PCT/GB2006/001895
§ 371 (c)(1),
(2), (4) Date: May 12, 2008

(87) PCT Pub. No.: WO2006/125977
PCT Pub. Date: Nov. 30, 2006

(65) Prior Publication Data
US 2009/0012022 A1    Jan. 8, 2009

(30) Foreign Application Priority Data

May 25, 2005 (GB) ................................ 0510612.5
May 25, 2005 (GB) ................................ 0510617.4
Aug. 6, 2005 (GB) ................................ 0516191.4
Aug. 6, 2005 (GB) ................................ 0516193.0

(51) Int. Cl.
*C07H 21/04* (2006.01)
*C12Q 1/68* (2006.01)
*C12N 5/00* (2006.01)
*C12N 15/11* (2006.01)
*C12N 5/02* (2006.01)

(52) U.S. Cl. .......... 536/24.5; 536/23.1; 435/6; 435/325; 435/375; 514/44 A

(58) Field of Classification Search ................. 536/24.5; 435/6, 375; 424/93.2; 514/44
See application file for complete search history.

(56) References Cited

U.S. PATENT DOCUMENTS

2003/0194718 A1* 10/2003 Tomita et al. ...................... 435/6
2003/0206887 A1* 11/2003 Morrissey et al. ........... 424/93.2
2004/0166553 A1* 8/2004 Nguyen et al. .................. 435/15
2006/0166913 A1* 7/2006 Suzuki ............................ 514/44

FOREIGN PATENT DOCUMENTS

| WO | WO 03008573 A2 * | 1/2003 |
| WO | WO 2004065415 A2 * | 8/2004 |
| WO | WO 2006/078798 A2 | 7/2006 |

OTHER PUBLICATIONS

Wang et al., A web-based design center for vector-based siRNA and siRNA cassette, 2004, Bioinformatics, vol. 20, pp. 1818-1820.*

Hung et al., Specific inhibition of gene expression and transactivation functions of hepatitis B virus X protein and c-myc by small interfering RNAs, 2004, FEBS Letters, vol. 560, pp. 210-214.*

Elbashir et al., Analysis of gene function in somatic mammalian cells using small interfering RNAs, 2002, Methods, vol. 26, pp. 199-213.*

Yoshinouchi et al., In vitro and in vivo growth suppression of human papillomavirus 16-positive cervical cancer cells by E6 siRNA, 2003, Molecular Therapy, vol. 8, pp. 762-768.*

Tang et al., Self-stabilized antisense oligodeoxynucleotide phosphorothioates: properties and anti-HIV activity, 1993, Nucleic Acids Research, vol. 21, pp. 2729-2735.*

Jiang, M., et al. A bi-functional siRNA construct induces RNA interference and also primes PCR amplification for its own quantification. Nucleic Acids Research. 2005, vol. 33, No. 18, p. e151.

Datta et al., "Direct Spectroscopic Study of Reconstituted Transcription Complexes Reveals That Intrinsic Termination Is Driven Primarily by Thermodynamic Destabilization of the Nucleic Acid Framework," Journal of Biological Chemistry, Feb. 8, 2008, vol. 283, No. 6, pp. 3537-3549.

McManus et al., "Gene silencing using micro-RNA designed hairpins," RNA, 2002, vol. 8, pp. 842-850.

Temiakov et al., "The specificity loop of T7 RNA polymerase interacts first with the promoter and then with the elongating transcript, suggesting a mechanism for promoter clearance," Proceedings of the National Academy of Sciences (PNAS), Dec. 19, 2000, vol. 97, No. 26, pp. 14109-14114.

* cited by examiner

*Primary Examiner* — Dana Shin
(74) *Attorney, Agent, or Firm* — Pabst Patent Group LLP

(57) ABSTRACT

The invention relates to a hybrid interfering RNA molecule comprising a duplex RNA and a single stranded DNA molecule and its use in the ablation of mRNA and in polymerase chain reactions.

37 Claims, 5 Drawing Sheets

HYBRID INTERFERING RNA

The invention relates to a hybrid interfering RNA molecule comprising a duplex RNA and a single stranded DNA molecule and including compositions and uses of said hybrid interfering RNA in RNA interference.

A number of techniques have been developed in recent years which claim to specifically ablate genes and/or gene products. For example, the use of anti-sense nucleic acid molecules to bind to and thereby block or inactivate target mRNA molecules is an effective means to inhibit gene expression. This is typically very effective in plants where anti-sense technology produces a number of striking phenotypic characteristics. However, antisense is variable leading to the need to screen many, sometimes hundreds of transgenic organisms carrying one or more copies of an antisense transgene to ensure that the phenotype is indeed truly linked to the antisense transgene expression. Antisense techniques, not necessarily involving the production of stable transfectants, have been applied to cells in culture, with variable results. In addition, the ability to be able to disrupt genes via homologous recombination has provided biologists with a crucial tool in defining developmental pathways in higher organisms. The use of mouse gene "knock out" strains has allowed the dissection of gene function and the probable function of human homologues to the deleted mouse genes.

A more recent technique to specifically ablate gene function is through the introduction of double stranded RNA, also referred to as small inhibitory or interfering RNA (siRNA), into a cell which results in the destruction of mRNA complementary to the sequence included in the siRNA molecule. The siRNA molecule comprises two complementary strands of RNA (a sense strand and an antisense strand) annealed to each other to form a double stranded RNA molecule. The siRNA molecule is typically derived from exons of the gene which is to be ablated.

The mechanism of RNA interference is being elucidated. Many organisms respond to the presence of double stranded RNA by activating a cascade that leads to the formation of siRNA. The presence of double stranded RNA activates a protein complex comprising RNase III which processes the double stranded RNA into smaller fragments (siRNAs, approximately 21-29 nucleotides in length) which become part of a ribonucleoprotein complex. The siRNA acts as a guide for the RNase complex to cleave mRNA complementary to the antisense strand of the siRNA thereby resulting in destruction of the mRNA.

The present invention relates to a modified siRNA molecule which is modified to include a single stranded DNA molecule extension which is adapted to allow the detection of siRNA in a sample.

We show that the modified siRNA-DNA construct (termed 'crook' siRNA) functions as a primer for the polymerase chain reaction (PCR), and describe a simple PCR protocol for its quantitation (amolar levels/cell). When transfected into mammalian cells crook siRNA induces selective mRNA knock-down equivalent to its unmodified siRNA counterpart. This new bi-functional siRNA construct will enable future studies on the uptake, distribution and pharmacokinetics of siRNA, and is particularly important for the development of siRNA-based therapeutics.

According to an aspect of the invention there is provided a hybrid nucleic acid molecule comprising a first part that comprises a duplex ribonucleic acid (RNA) molecule and a second part that comprises a single stranded deoxyribonucleic acid (DNA) molecule.

In a preferred embodiment of the invention said single stranded DNA molecule is contiguous with the sense strand of said duplex RNA molecule.

In an alternative preferred embodiment of the invention said single stranded DNA molecule is contiguous with the antisense strand of said duplex RNA molecule.

In a preferred embodiment of the invention said single stranded DNA molecule is extended and is contiguous with both sense and antisense strands of said duplex RNA molecule.

In a preferred embodiment of the invention said single stranded DNA molecule comprises a 3' terminal nucleic acid sequence wherein said sequence is adapted over at least part of its length to anneal by complementary base pairing to a part of said single stranded DNA to form a double stranded DNA structure.

In a preferred embodiment of the invention said single stranded DNA molecule comprises at least one copy of the sequence d (GCGAAGC). (SEQ ID NO:1).

In a preferred embodiment of the invention said single stranded DNA molecule is adapted to be resistant to nuclease digestion. Preferably said resistance is conferred by said double stranded DNA structure.

Typically said single stranded DNA molecule is at least 7 nucleotides in length. Preferably said single stranded DNA molecule is between 10-40 nucleotide bases in length, more preferably 15-30 nucleotides in length.

In a preferred embodiment of the invention said duplex RNA molecule is at least 18 base pairs in length.

In a further preferred embodiment of the invention said duplex RNA molecule is between 19 bp and 1000 bp in length. More preferably the length of said duplex RNA molecule is at least 30 bp; at least 40 bp; at least 50 bp; at least 60 bp; at least 70 bp; at least 80 bp; or at least 90 bp.

In a yet further preferred embodiment of the invention said duplex RNA molecule is at least 100 bp; at least 200 bp; at least 300 bp; at least 400 bp; at least 500 bp; at least at least 600 bp; at least 700 bp; at least 800 bp; at least 900 bp; or at least 1000 bp in length.

Preferably said duplex RNA molecule is between 18 bp and 29 bp in length. More preferably still said duplex RNA molecule is between 21 bp and 27 bp in length. Preferably said duplex RNA molecule is about 21 bp in length.

In a preferred embodiment of the invention said duplex RNA molecule encodes at least part of at least one gene, preferably a disease associated gene. Preferably said disease associated gene is a viral gene.

In a preferred embodiment of the invention said disease associated gene is a cancer associated gene. Preferably said cancer associated gene is an oncogene, preferably a viral oncogene.

In a preferred embodiment of the invention said viral gene is derived from a virus selected from the group consisting of: Human Immunodeficiency Virus; Human T Cell Leukaemia Virus; human papilloma virus; papovavirus; rhinovirus; poliovirus; herpesvirus; adenovirus; Epstein Barr virus; influenza virus, hepatitis B and C viruses.

In a preferred embodiment of the invention said viral gene is a papilloma virus gene, preferably a human papilloma virus gene.

Human papillomaviruses (HPV) vary in their pathological effects. For example, in humans so called low risk HPVs such as HPV-6 and HPV-11 cause benign hyperplasias such as genital warts, (also referred to as condyloma acuminata) while high risk HPVs, for example, HPV-16, HPV-18, HPV-31, HPV-33, HPV-52, HPV-54 and HPV-56, can cause cancers such as cervical or penile carcinoma. HPV-1 causes verruca vulgaris. HPV-5 and HPV-8 cause malignant squamous cell carcinomas of the skin. HPV-2 is found in malignant and non malignant lesions in cutaneous (skin) and squamous (oral) epithelium. HPV-16 is found associated with recurrent respiratory papillomatosis.

In a preferred embodiment of the invention said human papilloma virus is selected from the group consisting of: HPV-2; HPV-6; HPV-11; HPV-16, HPV-18, HPV-31, HPV-33, HPV-52, HPV-54; HPV-56; HPV-5 and HPV-8.

In a preferred embodiment of the invention said HPV is HPV-16.

In a preferred embodiment of the invention said viral gene is E6 or E7.

In a further preferred embodiment of the invention said hybrid nucleic acid molecule consists of a first part that consists of a duplex ribonucleic acid (RNA) molecule and a second part that consists of a single stranded deoxyribonucleic acid (DNA) molecule.

In a further preferred embodiment of the invention said hybrid nucleic acid molecule is modified.

The term "modified" as used herein describes a nucleic acid molecule in which;
i) at least two of its nucleotides are covalently linked via a synthetic internucleoside linkage (i.e., a linkage other than a phosphodiester linkage between the 5' end of one nucleotide and the 3' end of another nucleotide). Alternatively or preferably said linkage may be the 5' end of one nucleotide linked to the 5' end of another nucleotide or the 3' end of one nucleotide with the 3' end of another nucleotide; and/or
ii) a chemical group, such as cholesterol, not normally associated with nucleic acids has been covalently attached to the double stranded nucleic acid.
iii) Preferred synthetic internucleoside linkages are phosphorothioates, alkylphosphonates, phosphorodithioates, phosphate esters, alkylphosphonothioates, phosphoramidates, carbamates, phosphate triesters, acetamidates, peptides, and carboxymethyl esters.

The term "modified" also encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Thus modified nucleotides may also include 2' substituted sugars such as 2'-O-methyl-; 2-O-alkyl; 2-O-allyl; 2'-S-alkyl; 2'-S-allyl; 2'-fluoro-; 2'-halo or 2; azido-ribose, carbocyclic sugar analogues a-anomeric sugars; epimeric sugars such as arabinose, xyloses or lyxoses, pyranose sugars, furanose sugars, and sedoheptulose.

Modified nucleotides are known in the art and include, by example and not by way of limitation, alkylated purines and/or pyrimidines; acylated purines and/or pyrimidines; or other heterocycles. These classes of pyrimidines and purines are known in the art and include, pseudoisocytosine; N4, N4-ethanocytosine; 8-hydroxy-N6-methyladenine; 4-acetylcytosine, 5-(carboxyhydroxylmethyl)uracil; 5-fluorouracil; 5-bromouracil; 5-carboxymethylaminomethyl-2-thiouracil; 5 carboxymethylaminomethyl uracil; dihydrouracil; inosine; N6-isopentyl-adenine; 1-methyladenine; 1-methylpseudouracil; 1-methylguanine; 2,2-dimethylguanine; 2-methyladenine; 2-methylguanine; 3-methylcytosine; 5-methylcytosine; N6-methyladenine; 7-methylguanine; 5-methylaminomethyl uracil; 5-methoxy amino methyl-2-thiouracil; β-D-mannosylqueosine; 5-methoxycarbonylmethyluracil; 5-methoxyuracil; 2 methylthio-N-6-isopentenyladenine; uracil-5-oxyacetic acid methyl ester; psueouracil; 2-thiocytosine; 5-methyl-2 thiouracil, 2-thiouracil; 4-thiouracil; 5-methyluracil; N-uracil-5-oxyacetic acid methylester; uracil 5-oxyacetic acid; queosine; 2-thiocytosine; 5-propyluracil; 5-propylcytosine; 5-ethyluracil; 5-ethylcytosine; 5-butyluracil; 5-pentyluracil; 5-pentylcytosine; and 2,6,-diaminopurine; methylpsuedouracil; 1-methylguanine; 1-methylcytosine. Modified double stranded nucleic acids also can include base analogs such as C-5 propyne modified bases (see Wagner et al., Nature Biotechnology 14:840-844, 1996).

According to a further aspect of the invention there is provided a hybrid nucleic acid molecule according to the invention for use as a pharmaceutical.

According to a further aspect of the invention there is provided a composition comprising a hybrid nucleic acid molecule according to the invention. Preferably said composition is a pharmaceutical composition.

In a preferred embodiment of the invention said composition further includes a carrier.

When administered the compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents, such as chemotherapeutic agents which can be administered separately from the hybrid nucleic acid molecule according to the invention or in a combined preparation if a combination is compatible.

The therapeutics of the invention can be administered by any conventional route, including injection or by gradual infusion over time. The administration may, for example, be oral, intravenous, intraperitoneal, intramuscular, intracavity, subcutaneous, transdermal or transepithelial.

Preferably said hybrid nucleic acid molecule is combined with a carrier that facilitates the topical administration of the hybrid nucleic acid molecule according to the invention. An example of such a carrier system is described in our co-pending application WO2005/051431 the content of which is incorporated by reference.

In a preferred embodiment of the invention said composition includes an agent complexed or associated with said hybrid nucleic acid molecule to facilitate the delivery of the hybrid nucleic acid to a cell. Preferably said agent is a liposome, immuno-liposome, dendrimer or polylysine-transferrine-conjugate.

In a preferred embodiment of the invention said carrier is a gel or colloidal medium. For example, agar, agarose, or a hydrogel.

Hydrogels are amorphous gels or sheet dressings which are crosslinked and which typically consist of a polymer, a humectant and water in varying ratios. Hydrogels are known in the art and are commercially available. Examples of commercially available hydrogels are Tegagel™, Nu-Gel™ or FlexiGel™.

In a preferred embodiment of the invention said composition is substantially immobilised on a vehicle wherein said vehicle is adapted to facilitate the application of said composition to a cell or tissue.

A vehicle is a device that facilitates the delivery of the hybrid nucleic acid to cells and tissues and can be manufactured from porous and fibrous materials, woven and non-woven materials (e.g. bandages, gauze, plasters), or be a mucoadhesive gel.

The compositions of the invention are administered in effective amounts. An "effective amount" is that amount of a composition that alone, or together with further doses, produces the desired response. In the case of treating a particular disease, such as cancer, the desired response is inhibiting the progression of the disease. This may involve only slowing the progression of the disease temporarily, although more preferably, it involves halting the progression of the disease permanently. This can be monitored by routine methods.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The pharmaceutical compositions used in the foregoing methods preferably are sterile and contain an effective amount of a hybrid nucleic acid molecule according to the invention for producing the desired response in a unit of weight or volume suitable for administration to a patient. The response can, for example, be measured by determining regression of a tumour, decrease of disease symptoms, modulation of apoptosis, etc.

The doses of the hybrid nucleic acid molecule according to the invention administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits. It will be apparent that the method of detection of the hybrid nucleic acid according to the invention facilitates the determination of an appropriate dosage for a subject in need of treatment.

In general, doses of nucleic acids of between 1 nM-1 µM generally will be formulated and administered according to standard procedures. Preferably doses can range from 1 nM-500 nM, 5 nM-200 nM, 10 nM-100 nM. Other protocols for the administration of compositions will be known to one of ordinary skill in the art, in which the dose amount, schedule of injections, sites of injections, mode of administration (e.g., intra-tumour) and the like vary from the foregoing. The administration of compositions to mammals other than humans, (e.g. for testing purposes or veterinary therapeutic purposes), is carried out under substantially the same conditions as described above. A subject, as used herein, is a mammal, preferably a human, and including a non-human primate, cow, horse, pig, sheep, goat, dog, cat or rodent. Also within the scope of the invention are vectors that mediate the transmission of disease, for example mosquito transmission of malaria, yellow fever and Dengue fever, or tsetse fly transmission of sleeping sickness; the transmission of influenza by birds and pigs; the transmission of liver fluke by molluscs such as water snails in the control of schistosomiasis.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Compositions may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" in this context denotes an organic or inorganic ingredient, natural or synthetic, with which the active ingredient is combined to facilitate the application, e.g. liposome or immuno-liposome. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt. The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as syrup, elixir or an emulsion or as a gel. Compositions may be administered as aerosols and inhaled.

Compositions suitable for parenteral administration conveniently comprise a sterile aqueous or non-aqueous preparation of nucleic acid, which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

In a further preferred embodiment of the invention said pharmaceutical composition comprises at least one further therapeutic agent; preferably a chemotherapeutic agent.

In a further preferred embodiment of the invention said therapeutic agent is an antibody, preferably a monoclonal antibody or active binding fragment thereof.

Various fragments of immunoglobulin or antibodies are known in the art, i.e., Fab, Fab$_2$, F(ab')$_2$, Fv, Fc, Fd, scFvs, etc. A Fab fragment is a multimeric protein consisting of the immunologically active portions of an immunoglobulin heavy chain variable region and an immunoglobulin light chain variable region, covalently coupled together and capable of specifically binding to an antigen. Fab fragments are generated via proteolytic cleavage of an intact immunoglobulin molecule. A Fab$_2$ fragment comprises two joined Fab fragments. When these two fragments are joined by the immunoglobulin hinge region, a F(ab')$_2$ fragment results. An Fv fragment is multimeric protein consisting of the immunologically active portions of an immunoglobulin heavy chain variable region and an immunoglobulin light chain variable region covalently coupled together and capable of specifically binding to an antigen. A fragment could also be a single chain polypeptide containing only one light chain variable region, or a fragment thereof that contains the three CDRs of the light chain variable region, without an associated heavy chain variable region, or a fragment thereof containing the three CDRs of the heavy chain variable region, without an associated light chain moiety; and multi specific antibodies formed from antibody fragments, this has for example been described in U.S. Pat. No. 6,248,516. Fv fragments or single region fragments are typically generated by expression in host cell lines of the relevant identified regions. These and other immunoglobulin or antibody fragments are within the scope of the invention and are described in standard immunology textbooks such as Paul, *Fundamental Immunology* or Janeway et al. Immunobiology.

It is possible to create single variable regions, so called single chain antibody variable region fragments (scFvs). If a hybridoma exists for a specific monoclonal antibody it is well within the knowledge of the skilled person to isolate scFvs from mRNA extracted from said hybridoma via RT PCR. Alternatively, phage display screening can be undertaken to identify clones expressing scFvs. Alternatively, the fragments are "domain antibody fragments". Domain antibodies are the smallest binding part of an antibody (approximately 13 kDa). Examples of this technology is disclosed in U.S. Pat. No. 6,248,516, U.S. Pat. No. 6,291,158, U.S. Pat. No. 6,127,197 and EP0368684 which are all incorporated by reference.

According to a further aspect of the invention there is provided a cell transfected with a hybrid nucleic acid molecule according to the invention.

In a preferred embodiment of the invention said cell is a eukaryotic cell.

Preferably said eukaryotic cell is a mammalian cell, preferably a human cell.

In a preferred embodiment of the invention said cell is selected from the group consisting of: a nerve cell; a muscle cell; a liver cell; a kidney cell; a blood cell (e.g. erythrocyte, CD4+ lymphocyte, CD8+ lymphocyte, B-lymphocyte, dendritic cell, a panceatic β cell; an epithelial cell (e.g. lung, gastric); an endothelial cell; a fibroblast, an osteoblast, an osteoclast.

In a further preferred embodiment of the invention said cell is a stem cell.

In a preferred embodiment of the invention said stem cell is selected from the group consisting of: a mesenchymal stem cell, haemopoietic stem cell; neural stem cell; bone stem cell; muscle stem cell; trophoblastic stem cell; epithelial stem cell; derived from organs such as the skin, gastrointestinal mucosa, kidney, bladder, mammary glands, uterus, prostate and endocrine glands such as the pituitary; endodermal stem cells; derived from organs such as the liver, pancreas, lung and blood vessels; a pluripotent embryonic stem (ES) cell; a pluripotent embryonic germ (EG) cell; or a cell derived therefrom.

In a further preferred embodiment of the invention said eukaryotic cell is a fungal cell, for example a cell of the genus *Candida* spp (e.g. *C. albicans*) or *Saccharomyces* spp (e.g. *S. cerevisae*).

In a further preferred embodiment of the invention said cell is a parasitic cell, for example a nematode cell, cells of the genus *Leishmania* spp, *Trypanosoma* spp, *Schistosoma* spp or *Plasmodium* spp.

In a preferred embodiment of the invention said cell is a diseased cell.

In a further preferred embodiment of the invention said cell is a cancer cell.

In a preferred embodiment of the invention said cancer cell is selected from the group consisting of: a prostate cell; a cervical cell, a breast cell, a melanocyte, a hepatocyte, a kidney cell, glioma cell, bladder cell, lung cell, nerve cell, ovarian cell, testicular cell, pancreatic cell, gastrointestinal cell, lymphoma cell, seminoma, embryonal carcinoma, yolk sac carcinoma, choriocarcinoma, bone cell.

In an alternative preferred embodiment of the invention said cell is a plant cell.

In a preferred embodiment of the invention said plant cell is isolated from the plant species selected from the group consisting of: corn (*Zea mays*), canola (*Brassica napus, Brassica rapa* ssp.), alfalfa (*Medicago sativa*), rice (*Oryza sativa*), rye (*Secale cerale*), sorghum (*Sorghum bicolor, Sorghum vulgare*), sunflower (*helianthus annuas*), wheat (*Tritium aestivum*), soybean (*Glycine max*), tobacco (*Nicotiana tabacum*), potato (*Solanum tuberostum*), peanuts (*Arachis hypogaea*), cotton (*Gossypium hirsutum*), sweet potato (*Iopmoea batatus*), cassava (*Manihot esculenta*), coffee (*Cofea* spp.), coconut (*Cocos nucifera*), pineapple (*Anana comosus*), citris tree (*Citrus* spp.) cocoa (*Theobroma cacao*), tea (*Camellia senensis*), banana (*Musa* spp.), avacado (*Persea americana*), fig (*Ficus casica*), guava (*Psidium guajava*), mango (*Mangifer indica*), olive (*Olea europaea*), papaya (*Carica papaya*), cashew (*Anacardium occidentale*), macadamia (*Macadamia intergrifolia*), almond (*Prunus amygdalus*), sugar beets (*Beta vulgaris*), oats, barley, vegetables and ornamentals.

Preferably, plant cells of the present invention are isolated from crop plants (for example, cereals and pulses, maize, wheat, potatoes, tapioca, rice, sorghum, millet, cassava, barley, pea, and other root, tuber or seed crops. Important seed crops are oil-seed rape, sugar beet, maize, sunflower, soybean, and sorghum. Horticultural plants to which the present invention may be applied may include lettuce, endive, and vegetable brassicas including cabbage, broccoli, and cauliflower, and carnations and geraniums. The present invention may be applied in tobacco, cucurbits, carrot, strawberry, sunflower, tomato, pepper, and chrysanthemum.

In a preferred embodiment of the invention said cell is a transgenic cell, preferably a plant transgenic cell.

In an alternative preferred embodiment of the invention said cell is a prokaryotic cell, preferably a bacterial cell.

According to a further aspect to the invention there is provided a method to treat a disease or condition that would benefit from administration of a hybrid nucleic acid molecule comprising administering a therapeutically effective amount of said hybrid nucleic acid according to the invention to a subject in need of treatment.

In a preferred method of the invention said disease or condition is a genetically inherited disease.

In an alternative preferred method of the invention said disease caused by an infective agent.

In a preferred method of the invention said infective agent is selected from the group consisting of: a virus; a bacterium, a parasite, a fungus or a viroid.

In a preferred method of the invention said disease is cancer.

In a preferred method of the invention said cancer is selected from the group consisting of: cervical cancer, prostate cancer, a breast cancer, a melanoma, hepatoma, renal cancer, glioma, bladder cancer, lung cancer, cancer of the central nervous system, ovarian cancer, testicular cancer, cancer of the pancreas, gastrointestinal cancer, lymphoma, seminoma, embryonal carcinoma, yolk sac carcinoma, choriocarcinoma, osteocarcinoma.

In a preferred method of the invention said subject is human.

In an alternative preferred method of the invention said subject is an animal other than a human, for example a domestic animal.

According to a further aspect of the invention there is provided the use of a hybrid nucleic acid molecule comprising a first part that comprises a duplex ribonucleic acid (RNA) molecule and a second part that comprises a single stranded deoxyribonucleic acid (DNA) molecule as a primer for a polymerase chain reaction.

In a preferred embodiment of the invention said single stranded DNA molecule is contiguous with the sense strand of said duplex RNA molecule.

In an alternative preferred embodiment of the invention said single stranded DNA molecule is contiguous with the antisense strand of said duplex RNA molecule.

In a further preferred embodiment of the invention said single stranded DNA molecule is extended and is contiguous with both sense and antisense strands of said duplex RNA molecule.

In a further preferred embodiment of the invention said single stranded DNA molecule comprises a 3' terminal nucleic acid sequence wherein said sequence is adapted over at least part of its length to anneal by complementary base pairing to a part of said single stranded DNA to form a double stranded DNA structure.

In a preferred embodiment of the invention said single stranded DNA molecule comprises at least one copy of the sequence d (GCGAAGC). (SEQ ID NO: 1)

In a preferred embodiment of the invention said single stranded DNA molecule is adapted to be resistant to nuclease digestion. Preferably said resistance is conferred by said double stranded DNA structure.

Typically said single stranded DNA molecule is at least 7 nucleotides in length. Preferably said single stranded DNA molecule is between 10-40 nucleotide bases in length, more preferably 15-30 nucleotides in length.

In a preferred embodiment of the invention said duplex RNA molecule is at least 19 base pairs in length.

In a further preferred embodiment of the invention said duplex RNA molecule is between 20 bp and 1000 bp in length. More preferably the length of said duplex RNA molecule is at least 30 bp; at least 40 bp; at least 50 bp; at least 60 bp; at least 70 bp; at least 80 bp; or at least 90 bp.

In a yet further preferred embodiment of the invention said duplex RNA molecule is at least 100 bp; at least 200 bp; at least 300 bp; at least 400 bp; at least 500 bp; at least at least 600 bp; at least 700 bp; at least 800 bp; at least 900 bp; or at least 1000 bp in length.

Preferably said duplex RNA molecule is between 18 bp and 29 bp in length. More preferably still said duplex RNA molecule is between 21 bp and 27 bp in length. Preferably said duplex RNA molecule is 21 bp in length.

According to a further aspect of the invention there is provided a method to detect the presence of interfering RNA in a sample comprising the steps of:
  i) forming a preparation comprising a hybrid nucleic acid molecule comprising a first part that comprises a duplex RNA molecule and a second part that comprises a single stranded DNA molecule extension wherein said single stranded DNA molecule is adapted to anneal to a template nucleic acid molecule by complementary base pairing and to function as a first primer for a polymerase chain reaction; a second DNA molecule adapted to anneal to said template and function as a second primer for a polymerase chain reaction; a template nucleic acid; a thermostable DNA polymerase; and polymerase chain reaction components including nucleoside triphosphates;
  ii) providing reaction conditions that allow the amplification of said template nucleic acid by said first and second primer DNA molecules;
  iii) detecting the amplified product of the polymerase chain reaction.

Preferably said second DNA molecule is adapted to anneal to said template at a different site from said hybrid nucleic acid molecule.

In a preferred method of the invention said template is a DNA molecule.

In a further preferred method of the invention said DNA template is a DNA genetically engineered into a vector, for example a plasmid.

In a further preferred method of the invention said first primer comprises a 3' terminal nucleic acid sequence wherein said sequence is adapted over at least part of its length to anneal by complementary base pairing to a part of said single stranded DNA to form a double stranded DNA structure.

According to a yet further aspect of the invention there is provided a kit comprising a hybrid nucleic acid molecule comprising a first part that comprises a duplex RNA molecule and a second part that comprises a single stranded DNA molecule wherein said single stranded DNA molecule is adapted to anneal to a template nucleic acid molecule by complementary base pairing and to function as a first primer for a polymerase chain reaction.

In a preferred embodiment of the invention said kit includes at least one further DNA molecule that functions as a second DNA primer for a polymerase chain reaction.

In a preferred embodiment of the invention said kit includes a nucleic acid template.

Preferably said kit comprises a thermostable DNA polymerase and components required for conducting the amplification of template nucleic acid. Preferably said kit includes a set of instructions for conducting said polymerase chain reaction.

According to a further aspect of the invention there is provided a polymerase chain reaction preparation comprising a hybrid nucleic acid molecule wherein said molecule comprises a first part that comprises a duplex ribonucleic acid (RNA) molecule and a second part that comprises a single stranded deoxyribonucleic acid (DNA) molecule wherein said molecule functions as a first primer in a polymerase chain reaction.

In a preferred embodiment of the invention said preparation comprises a second DNA molecule that functions as primer in a polymerase chain reaction.

In a further preferred embodiment of the invention said preparation comprises a nucleic acid template.

In a preferred embodiment of the invention said preparation comprises a thermostable DNA polymerase and polymerase chain reaction components including nucleoside triphosphates.

According to a further aspect of the invention there is provided a device for conducting a polymerase chain reaction wherein said device comprises a preparation according to the invention.

In a preferred embodiment of the invention said device is a thermo-cycling machine.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF DESCRIPTION OF DRAWINGS

An embodiment of the invention will now be described by example only and with reference to the following Figures.

MATERIALS AND METHODS

Construction of Crook DNA Template

Figure 1:
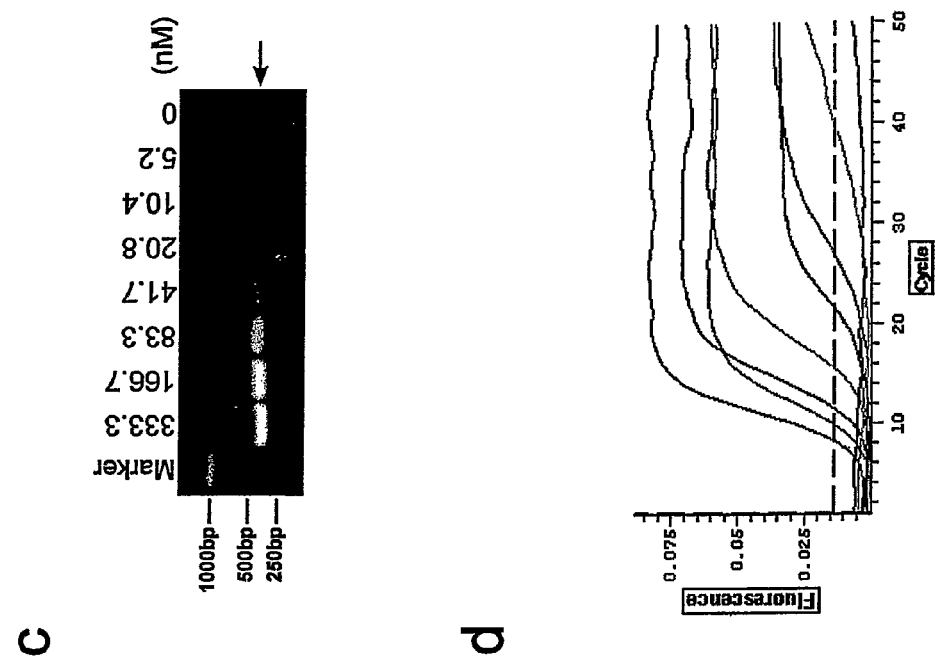
FIG. 1: Design and application of E7 crook siRNA for use in quantitative PCR. (a) Sequence (SEQ ID NO: 15) and schematic representation of E7 crook siRNA. (b) Design of the crook template and positions of upstream (E7 crook siRNA) and downstream primer (crook dn 7) for PCR amplification. The crook template (312 bp) is derived from the CMV promoter and is cloned into pBlueScript (pBS) to give pBS Crook (Methods). (c) Visualisation of crook template DNA following PCR amplification using E7 crook siRNA and crook dn 7 as primers and agarose gel electrophoresis. E7 crook siRNA was added in a limiting dilution series, as indicated; crook template and crook dn7 primer were present in excess for the reaction (see text). (d) Read-out from quantitative PCR showing effects of E7 crook siRNA dilution series (333.3 nM to 5.2 nM) on product amplification and plateau levels (see text).
Figure 1:
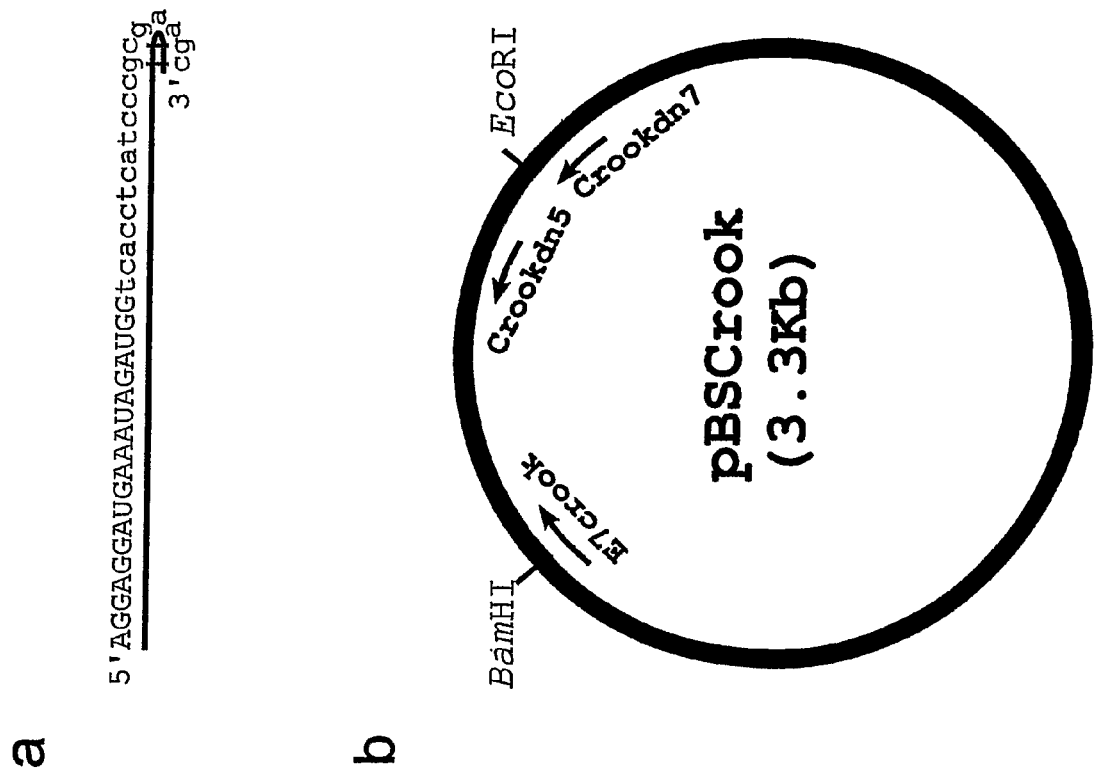

Forward primer 1 that contained crook sequence at the 5'-end (5'tcacctcatcccgcgaagcccatatatggagttcc3') (SEQ ID NO: 2) and reverse primer 1 (5'agcgatgactaatacgtagatgtac3') (SEQ ID NO: 3) were used to amplify the primary crook template from the CMV promoter sequence. The final crook DNA template was amplified with forward primer 2 (5'cgcggatcctcacctcatcccgcga3') (SEQ ID NO: 4) and reverse primer 2 (5'gcggaattcaagtaggaaagtcccataaggt3') (SEQ ID NO: 5) and cloned into pBS at BamHI/EcoRI, as pBSCrook (FIG. 1b). The PCRs were performed using Qiagen Hotstart PCR kit and the cycle as follows: 95° C., 15 min, 30 cycles of 94° C., 45 sec, 58° C., 45 sec, 72° C., 1 min, then 72° C. for 5 min. In pBSCrook template, there are two downstream primers usable for E7crook detection, designated crook dn5 (5'gtcaataggggggcgtacttg3') (SEQ ID NO: 6) and crook dn7 (5'gtaatacgactcactatagggcgaattggg3') (SEQ ID NO: 7), which give single products of 250 nt and 400 nt respectively.

Cell Culture and Transfection

Human HPV-16 positive cell line SiHa was cultured with MEM plus 10% FCS (Sigma), 1.0 mM Sodium pyruvate, and 0.1 mM non-essential amino acids. Human colorectal carcinoma HCT116 cells were cultured in DMEM with 10% FCS. HeLa cells containing stably integrated HIV-1 Tat gene under the Tet-Off promoter, firefly luciferase gene under HIV-1 LTR and *Renilla* luciferase gene under CMV promoter as described previously[13] were cultured as exponentially growing subconfluent monolayers on plates in DMEM medium supplemented with 10% Tet System Approved FBS (Clonetech). All the cell lines were maintained with Penicillin 100 units ml$^{-1}$ and streptomycin 100 μg ml$^{-1}$ at 37° C. in a 5% $CO_2$ incubator.

Total RNA Preparation

The transfected cells were washed three times with PBS, and harvested by trypsinization. The cells were counted and washed with PBS, following centrifugation at 200 g for 5 min to pellet. The cell pellets were lysed in Lysis buffer A (140 mM NaCl, 10 mM Tris, 0.5% NP-40, pH8.0) on ice for 10 min. The lysis solutions were extracted with 1:1 volume of Phenol once and 1:1 volume of Chloroform/isoamyl alcohol (24:1) once. The total RNA were precipitated by adding 1/10 volume 3M NaOAc (pH5.2), 1 μl Glycoblue (Ambion) and 2.5 volume of ice-cold 100% ethanol at −20° C. for at least 1 hour. After centrifugation at 13,000 rpm, 4° C. for 30 min, the RNA pellets were washed once with 75% ice-cold ethanol, dried and resuspended in 100 μl RNase/DNase-free ddH$_2$O.

Detection of E7 Crook siRNA by Real-Time PCR

Figure 2:
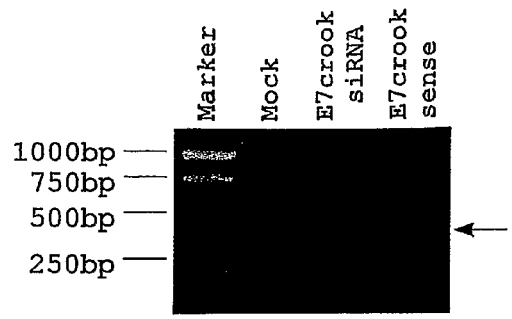
FIG. 2: Recovery and quantitation of E7 crook siRNA following transfection into human cells in culture. (a) Recovery of E7 crook siRNA duplex and also of single stranded E7 crook siRNA sense strand at 24 h and 72 h after transfection in to SiHa cells visualised indirectly by its ability to prime the amplification of the crook template. Parallel cell cultures were transfected with either duplex E7 crook siRNA or with single-stranded E7 crook sense RNA, as indicated. (b) Quantitation of E7 crook siRNA (red triangles) using standard curves derived from a dilution series of E7 crook siRNA (Methods); internal standard dilution curves were performed for each experiment). E7 crook siRNA was recovered with total RNA 24 h following transfection into either SiHa or HCT116 cells, as indicated. (c) Recovery levels of E7 crook siRNA at 24 h, 48 h and 72 h post-transfection into SiHa and HCT116 cells as indicated.
Figure 2:
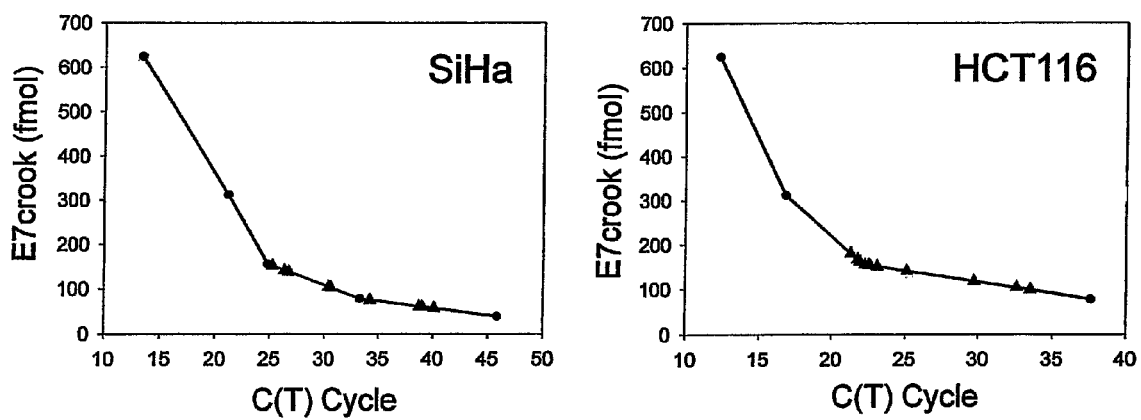
Figure 2:
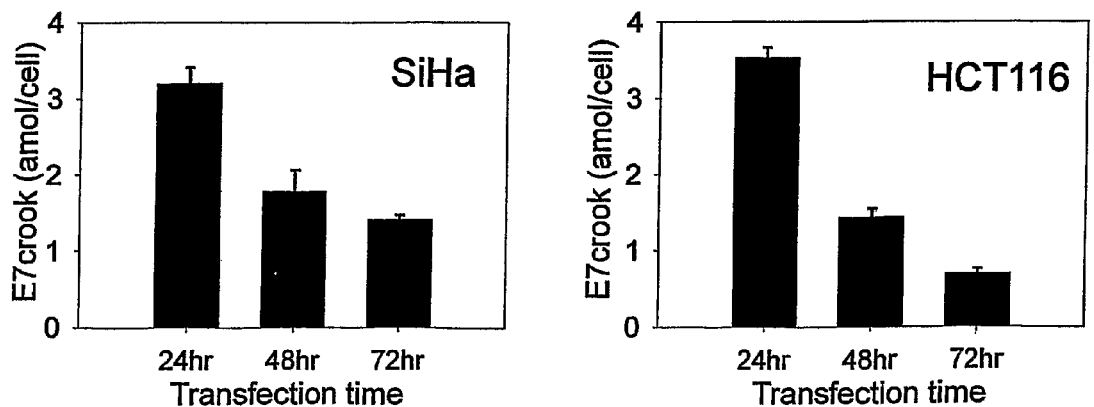

The real-time PCRs were performed using DNA Engine Opticon 2 System (MJ Research, USA) and QuantiTect SYBR Green PCR kit (Qiagen, UK). In each reaction, the final concentration of pBSCrook template and downstream primer Crook dn7 are: 200 pg/μl and 0.33 μM respectively. For the standard curve, the input of E7 crook was diluted from 333.3 nM to 5.2 nM (FIG. 1c). The cycle was: 94° C., 15 min, 50 cycles of 94° C., 45 sec, 60° C., 45 sec, 72° C., 45 sec. For detection of E7 crook in transfected cells, 500 ng of total RNA was used in each reaction. For E7 crook dose dependent detection, 1 μg total RNA was used for each reaction. All quantitation statistics were calculated using Sigma plot 8.0. The standard curves were plotted as shown in FIG. 2b. The equation for quantitation of E7 crook in transfected cells is: $Y_i=Y_1+(X_i-X_1)\times(Y_2-Y_1)/(X_2-X_1)$ where X: C(T) cycle value, and Y: E7 crook amount value.

RNA Interference as Evidenced by mRNA Knock-Down and Cellular Phenotype.

siRNAs (see FIG. 1 and Ref. 11) were synthesised and HPLC purified (Dharmacon). For annealing of the siRNAs, 20 μM complementary RNAs were incubated in annealing buffer (20 mM Tris-HCl pH7.5; 10 mM MgCl; and 50 mM NaCl) for 1 min at 90° C. followed by 1 hr at 37° C. For transfection the SiHa and HCT116 cells were trypsinised and subbed into 6 well plates (10 cm$^2$) without antibiotics, 1.5× 10$^5$ cells per well. After 24 h the cells were transfected with siRNA formulated into liposomes (Oligofectamine, Life Technologies) according to the manufacturer's instructions. siRNA concentration was 0.58 μg per 1.5×10$^5$ cells per well (equivalent to 200 nM). In nM, 40 nM, 8 μM, 1.6 nM to 0.32 nM addition an siRNA dilution series from 200 was performed. The final volume of culture medium was 1.5 ml per well. Cells were harvested for analysis at various times thereafter as indicated in the results. Each experiment was carried out four or more times. Transfection efficiencies were established by transfecting with liposomes containing FITC-dextran (FD-150; Sigma). For E7 mRNA amplification by real-time PCR the primers were 5'-CGGAATTCATGCATGGAGATACACCTACAT-3' (SEQ ID NO: 8) and 5'-CGGGAAGCTTATGGTTTCTGAGAA-CAGATGG-3'(SEQ ID NO: 9), and the thermal cycle was 47° C., 30 min; 94° C., 2 min; then 30 cycles of 94° C. 45 sec, 58° C. 45 sec and 72° C. 2 min; followed by 72° C., 5 min. For lamin A/C mRNA amplification the primers 5'-AAG-CAGCGTGAGTTTGAGAGC-3' (SEQ ID NO: 10) and 5'-AGGGTGAACTTTGGTGGGAAC-3' (SEQ ID NO: 11) were used in the thermal cycle: 50° C. 30 min, 94° C. 15 min, then 30 cycles of 94° C. 45 sec, 58° C. 45 sec, 72° C. 1 min, followed by 80° C. 15 sec. For cell cycle analysis the cells were harvested, washed with PBS and fixed in 90% ethanol overnight at −20° C. The fixed cells were pelleted, washed in PBS and resuspended in PBS containing 0.1 μg/ml propidium iodide with 200 U/ml RNase A and analysed by FACS. Apoptotic cells were identified using annexin-V-Fluos (Boehringer) following the manufacturer's protocol.

RNA Interference as Evidenced by the Luciferase Assay.

siRNA's comprising the following sense strands were used (5'-3'): GL3-FFL siRNA[15]—CUUACGCUGAGUACUUC-GAtt (SEQ ID NO: 12); GL3-FFL crook siRNA CUUACGCUGAGUACUUCGAtcacctcatcccgcgaagc; GL3-FFL mism siRNA—CGUACGCGGAAUACUUCGAtt (SEQ ID NO: 14); and as a negative siRNA control—non specific control VI (Dharmacon). To assess RNA interference a dual luciferase reporter assay was used. In each experiment, two identical 96 well plates were prepared with 10$^4$ HeLa Tet-Off/Tat/luc-f/luc-R cells per well and incubated at 37° C. for 24 h. One of the plates was used for the luciferase assay and the other for the cytotoxicity assay. After annealing in Dharmacon siRNA buffer, siRNA's were prepared at a concentration of 500 nM in Opti-MEM (Invitrogen) serum-free medium and formed a complex with a 1:200 volume of Lipofectamine 2000 (Invitrogen). After 20 min at room temperature, subsequent dilutions were prepared from siRNA/Lipofectamine 2000 mixture. Cells were incubated with the mixtures for 3 h, washed with phosphate buffered saline and left for additional incubation in DMEM/10% FBS for 24 h. Cell lysates were prepared and analysed using the Dual Luciferase Reporter Assay System (Promega) and relative light units for both firefly and *Renilla* luciferase read sequentially using a Berthold Detection Systems Orion Microplate luminometer. Toxicity was determined by measurement of the proportion of live cells colorimetrically using CellTiter 96 AQ$_{ueous}$ One Solution Assay (Promega). The absorbance at 490 nm was read using a Molecular Devices Emax microplate reader. Each data point was averaged over two replicates of three separate experiments.

Example 1

The aim of this work was to construct a siRNA derivative that (i) enables its detection by PCR-based technology and (ii) retains RNAi activity for selective knock-down of targeted mRNA in mammalian cells. Our approach was to modify the sense strand of the siRNA duplex to enable its use as a primer for the PCR reaction. Accordingly the 3' end of the sense strand of siRNA (21 nucleotides, nts) was extended into a 19-nt DNA sequence to function as PCR primer. The end of the DNA primer sequence, d(GCGAAGC) (SEQ ID NO:1), forms a stable hairpin structure and confers nuclease resistance[4-8]. This siRNA-DNA structure is envisaged as a shepherd's crook and is termed crook-siRNA. As biological model for testing the ability of crook siRNA to induce RNAi we used a line of human cervical cancer cells (SiHa) positive for human papilloma virus type 16 (HPV16)[9]. These cells express viral E6 and E7 genes and we used E7 siRNA[10] as foundation for the construction of E7 crook siRNA (FIG. 1a) (SEQ ID NO: 15). First we tested the ability of E7 crook siRNA to function as a primer for PCR amplification of DNA.

The PCR reaction is routinely employed to detect and to quantitate a DNA template (or RNA template via reverse transcription) by cyclical amplification in vitro. The sample containing the DNA template is first heated to separate the complementary strands of DNA, including those of the DNA template of interest. Two opposing DNA primers are included which are designed to complement two defined sequences within the DNA template and separated by a known distance. These upstream and downstream primers serve to initiate synthesis of a DNA product of predicted length, synthesis being dependent upon the presence of the template. Importantly, the two PCR primers are added in excess for the reaction.

In the present study we have altered this standard PCR protocol to allow for a limiting quantity of the E7 crook siRNA (upstream) primer. Thus the E7 crook siRNA primer is limiting for the reaction, whilst the second (downstream) primer and the DNA template are added in excess for the reaction. Under these conditions it was predicted that the initial rate of template amplification would correlate with the initial concentration of the E7 crook siRNA primer. It was also anticipated that, during the repeated cycles of the PCR process, the E7 crook siRNA primer would become diluted to the point where it could no longer support the priming of new strand DNA synthesis, even though the downstream primer and the DNA template remain in excess (represented schematically in FIG. 1b): at this point template amplification should plateau.

The design of the E7 crook siRNA (sense strand) and the crook DNA template is shown schematically (FIGS. 1a,b). The crook DNA template is derived from the cytomegalovirus (CMV) promoter sequence and, for ease of production and general accessibility, is cloned into pBlueScript (pBS) to give the pBSCrook plasmid (3.3 kb; Methods). The ability of E7 crook siRNA to support PCR was demonstrated using crook dn7 (FIG. 1b) as downstream primer. Upon amplification a single PCR product of 400 base pairs was observed (FIG. 1c).

To test the sensitivity of the reaction we employed a dilution series of E7 crook siRNA ranging from 333.3 nM down to 5.2 nM. An excess of downstream DNA primer (crook dn7) and crook template was used throughout (Methods). A single melting point spanning 81.5° C. to 83° C. was obtained (not shown) and, as predicted, the product yield tended to plateau at lower levels with increasing dilution of the E7 crook siRNA primer (FIG. 1d). A single PCR product (400 nt) was detectable, even down to 5.2 nM E7 crook siRNA (FIGS. 1c, d). Similar sensitivity has been obtained using a more complex, radioactive method for the detection of siRNA[11]. Briefly, liquid hybridisation with a $^{32}$P-labelled probe is followed by a nuclease protection step and the resultant samples are analysed by polyacrylamide gel electrophoresis and blotting onto nylon membrane. A phosphorimager is used to detect and to quantitate the radioactive signal on the blots. Our approach carries the advantage of avoiding the use of radioactivity and exploits the simple principles of PCR. Thus crook siRNA may be employed to explore aspects of RNA interference that have hitherto proved problematic for study due to the very low levels of siRNA involved. With this objective in mind we next asked if crook siRNA can be recovered from cells and quantitated in the presence of cellular RNA.

Example 2

Previously we have shown that routine transfection of E7 siRNA into SiHa cervical cancer cells induces growth arrest and apoptosis[10]. In contrast, the growth and viability of non-viral infected cells, such as normal human diploid fibroblasts and HCT116 human colorectal cancer cells, are unaffected by E7 siRNA[10]. Using SiHa and HCT116 cells we now asked if E7 crook siRNA can be recovered from cells after liposomal transfection (the percentage cells transfected was between 70%-80% for both SiHa and HCT116 cells). Following transfection the cells were harvested at various times up to 72 hours and total RNA was extracted as described in the Methods. Care was taken to wash the cells extensively before lysis, thus removing unincorporated liposomal/crook siRNA complexes prior to cellular RNA extraction. A single product of the expected size was obtained by quantitative PCR (see FIG. 2a for SiHa samples). Parallel controls show that the single-stranded E7 crook siRNA (sense strand) is also recoverable up to at least 72 hours following transfection into SiHa cells and amplifies to give a single PCR product (FIG. 2a). This is important since it demonstrates that the crook siRNA sense strand is stable in cells. This stability is probably attributable to the DNA hairpin structure d(GCGAAGC) which is known to be nuclease resistant and thermostable[5-9]. In the context of RNA interference the detection of crook sense siRNA is likely to reflect crook siRNA duplexes plus crook sense siRNA that has been unwound and dissociated from the antisense strand during RISC complex formation.

The amount of E7 crook siRNA recovered from transfected cells was calculated using the standard curve derived from quantitative PCR of known dilutions of E7 crook siRNA (ranging from 333.3 nM to 5.2 nM; FIG. 2b). Samples were analysed in triplicate and the recovery of E7 crook siRNA from both the SiHa and HCT116 cells was remarkably reproducible (FIG. 2b). At 24 hr post-transfection similar amounts of E7 crook siRNA were recovered from the SiHa and the HCT116 cells (FIG. 2c). Subsequently the two cell lines differed as follows. The recovery level from HCT116 cells fell by approximately half during each 24 hr period (FIGS. 2c; 48 hr and 72 hr time points). This corresponds with the doubling time of this cell line and is likely to reflect dilution of the transfected E7 crook siRNA with each cell division. In contrast, E7 crook siRNA levels in the SiHa cells showed little decline after 48 hr (FIG. 2c). This is consistent with the transient growth arrest normally induced by E7 siRNA prior to apoptosis of the SiHa cervical cancer cells[10]. It is also confirms stability of the crook siRNA construct under the experimental conditions. Interestingly, the level of E7 crook siRNA recovery at 24 hr post-transfection indicates a very low up-take by the cells, i.e. less that 2% of total administered in the liposomal formulation. Recovery of crook siRNA from cells transfected with either 200 nM, 40 nM, 8 µM, 1.6 nM or 0.32 nM was also tested. Crook siRNA was readily detectable down to 1.6 nM input dose.

Example 3

Figure 3:
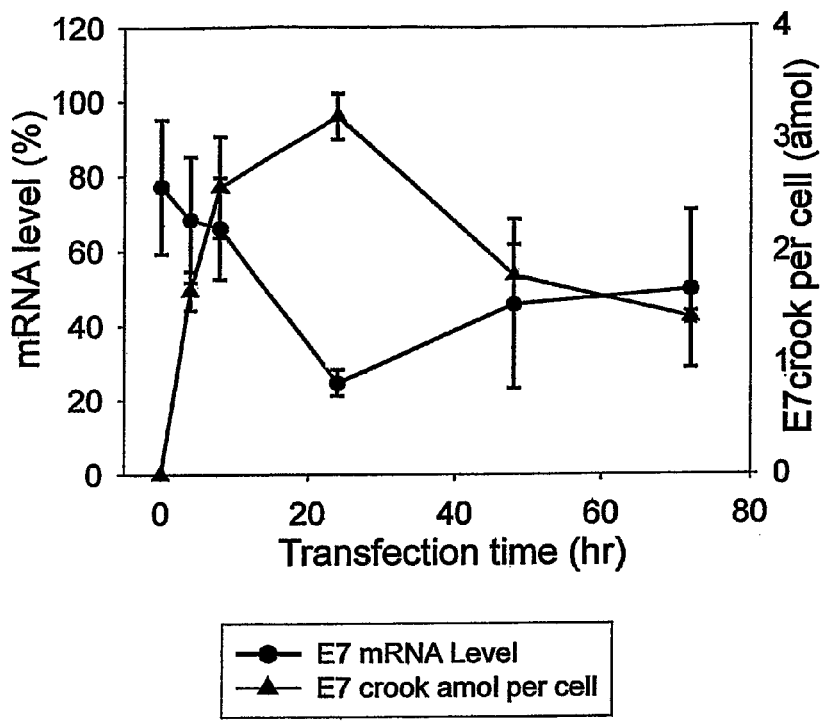
FIG. 3: RNA interference induced by crook siRNA. (a) Cellular levels of E7 crook siRNA (red dashed line) and E7 mRNA (solid black line) in SiHa cervical cancer cells at different times following a single transfection of the E7 crook siRNA. Cells were harvested for analysis at 0 h, 4 h, 5 h, 24 h, 48, and 72 h post-transfection. (b) Comparison of E7 mRNA knock-down by E7 crook siRNA and by unmodified E7 siRNA at 24 h, 48 h and 72 h post-transfection into SiHa cells. Also shown are lamin A/C mRNA levels, included as non-target negative control for E7 siRNA selectivity. (c) Comparison of Firefly Luciferase activity for GL3-FFL siRNA and GL3-FFL crook siRNA, with controls of GL3-FFL mismatched siRNA and non-specific siRNA (normalised to cell count). (d) Appearance of SiHa cervical cancer cells (expressing HPV E7 mRNA) and HCT116 colorectal cancer cells (negative for HPV E7 mRNA) 72 h post-transfection with E7 crook siRNA or with unmodified E7 siRNA, as indicated. Apoptosis of SiHa cells transfected with E7 siRNA was confirmed by annexin V staining and FACS analysis.
Figure 3:
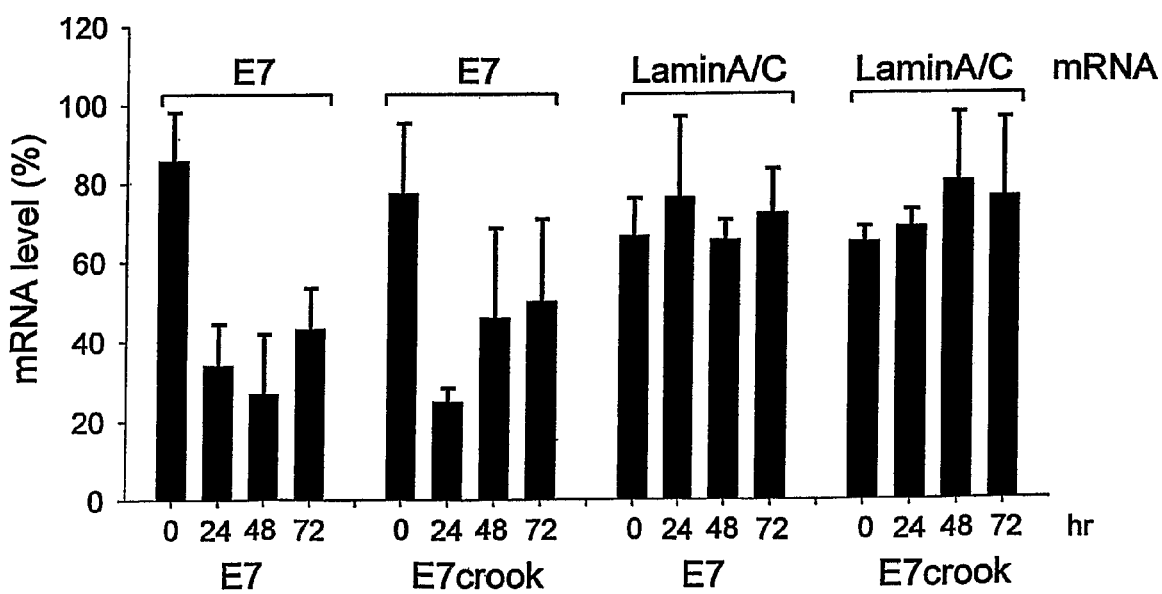

To ascertain if E7 crook siRNA is competent for induction of RNA interference we tested for selective knock-down of viral E7 mRNA in the SiHa cells (FIG. 3a and Methods). E7 mRNA knock-down following transfection with E7 crook siRNA was clearly evident at 24 h post-transfection with E7 crook siRNA (FIG. 3a). To determine if knock-down was selective for E7 mRNA we also measured lamin A/C mRNA levels. The results show that lamin A/C mRNA is unaffected by E7 crook siRNA at all time points tested (0 hr, 4 hr, 8 hr, 24 hr, 48 hr, and 72 hr; see FIG. 3b). We therefore conclude that E7 mRNA knock-down reflects selective targeting by E7 crook siRNA, rather than general non-selective mRNA degradation. Quantitation of E7 crook siRNA in these same samples reveals that maximal uptake occurs within 24 hr and shows a reciprocal correlation between cellular crook E7 siRNA and E7 mRNA levels (FIG. 3a).

Example 4

We were also interested to compare the effects of E7 crook siRNA with unmodified E7 siRNA. Parallel cultures of SiHa cells were transfected with either E7 crook siRNA or unmodified E7 siRNA, and harvested for analysis at 24 h, 48 h and 72 h post-transfection. The results obtained for E7 mRNA knock-down were essentially the same for both E7 crook siRNA and the unmodified E7 siRNA (FIG. 3b). Thus we conclude that crook siRNA (i) retains the ability to induce RNAi and (ii) appears to be functionally comparable with unmodified siRNA.

Example 5

Figure 3C:
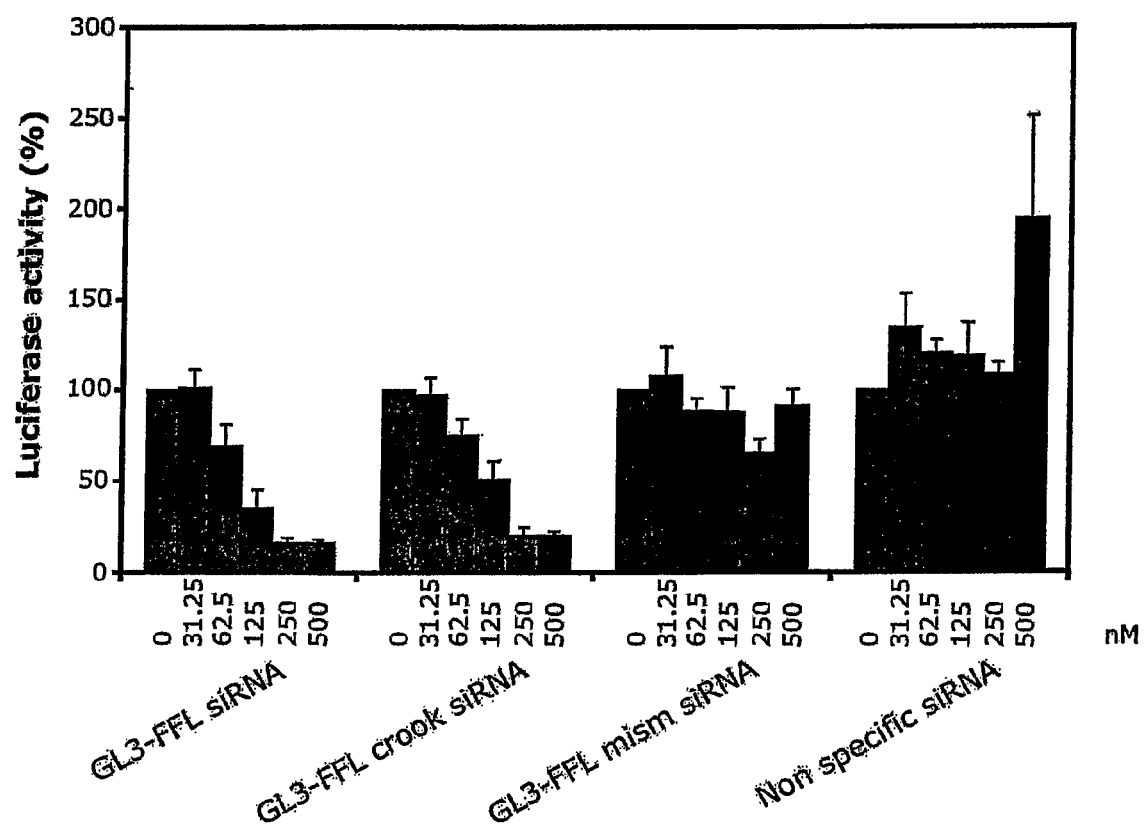
Figure 3:
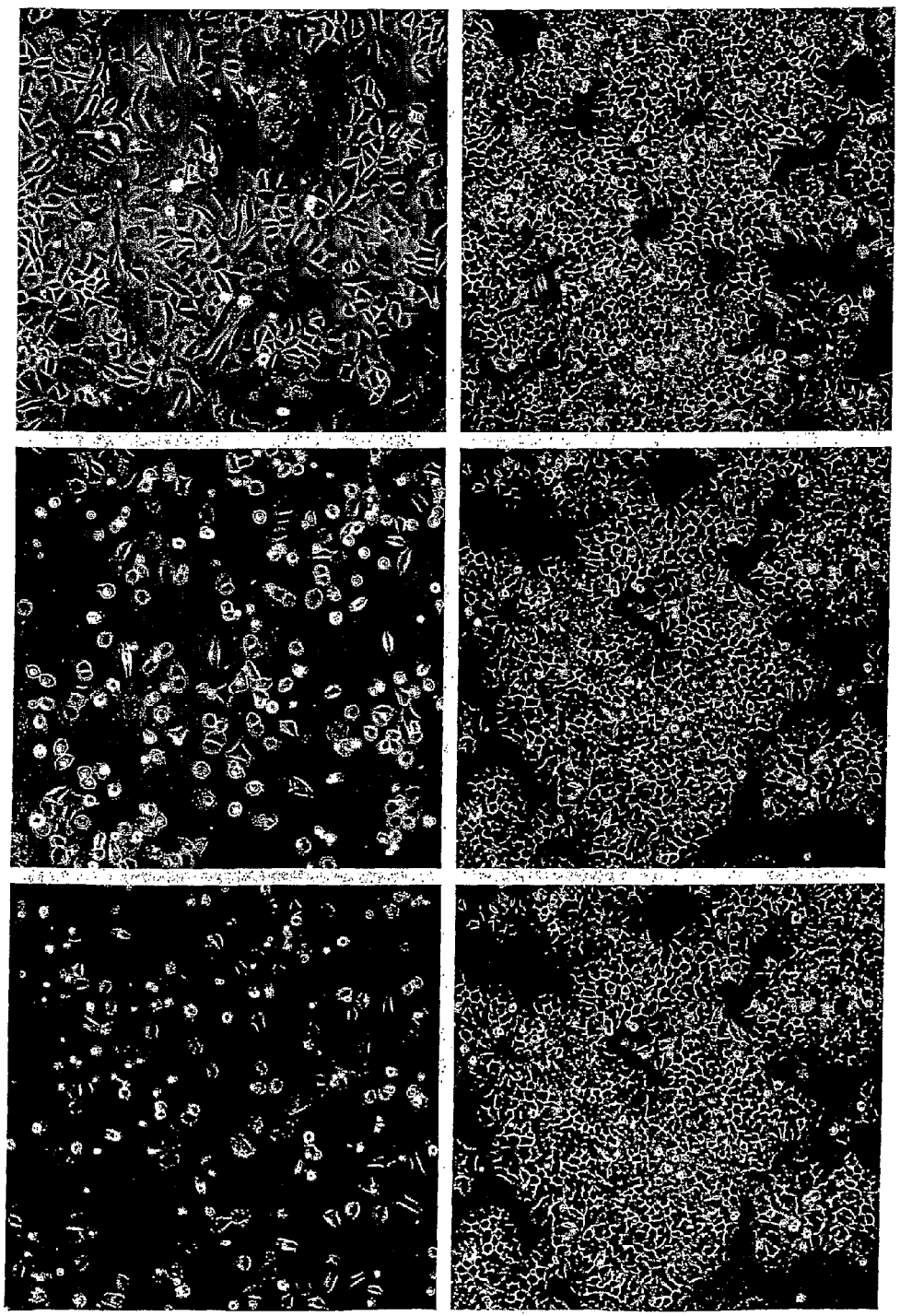

RNAi competency of crook siRNA was confirmed using a second, independent assay in which reporter plasmids are used to detect post-transcriptional gene silencing indirectly. Briefly, the assay employed HeLa cells encoding a stably integrated exogenous expression vector for GF3-firefly luciferase (GF3-FFL) under control of the HIV-1 promoter[12-14]. When transfected with GF3-FFL siRNA (19 nt) a dose dependent reduction in luciferase activity is observed (see, for example, FIG. 3c). Here we show that GF3-FFL crook siRNA (Methods) gives a similar dose response to that obtained with the unmodified GF3-FFL siRNA for the knock-down of luciferase activity (FIG. 3c and Methods). As expected, mismatch siRNA gave no reduction in luciferase activity (FIG. 3c). A second specificity control employed Renilla luciferase constitutively expressed under the CMV promoter (Ref). Again as expected, no reduction in Renilla luciferase activity was observed following transfection with either GF3-FFL crook siRNA or the unmodified GF3-FFL siRNA (data not shown). Thus we demonstrate equivalent functionality for crook siRNA and unmodified siRNA in two independent experimental models for induction of RNA interference in mammalian cells.

Example 6

Although SiHa cells express exogenous viral genes, this nonetheless reflects natural gene expression and HPV infection and viral gene expression are causal for cancerous transformation of cervical epithelial cells in vivo. Previously we have identified HPV E7 as survival factor for HPV16-positive cervical cancer cells[11] and shown that a single dose of E7 siRNA induces apoptosis in SiHa cervical cancer cells, evident 72 hr post-transfection. We now show that a single dose of E7 crook siRNA similarly induces apoptosis in the SiHa cells (FIG. 3d; upper panel). We observed induction of SiHa cell apoptosis down to 8 nM (not shown) and were able to recover and quantitate the crook siRNA at these low levels of input (see above; FIG. 2a). Lower input levels were also detectable (not shown) but were ineffective for induction of apoptosis.

In contrast, apoptosis was not observed in parallel cultures of HCT116 cells (which lack HPV E7 mRNA) (FIG. 3d; lower panel). Thus we substantiate the phenotypic consequences of E7 knock-down by RNA interference, and also demonstrate that the crook siRNA construct is not intrinsically cytotoxic for human epithelial cells (HCT116).

Since crook siRNA is designed to be bi-functional, with RNA interference initiated by the siRNA component of the molecule and PCR priming conferred by the crook DNA extension (see above), an important aspect of this novel technology is its ease of adaptation for use with siRNAs in general. Given the similarities between crook siRNA and unmodified siRNA for the induction of RNA interference (this work; FIGS. 3b,c) we anticipate that simple PCR-based detection and quantitation of crook siRNA will prove valuable in the development of RNAi therapeutics and informative on siRNA cellular up-take, tissue distribution and pharmacokinetics. However, the applications of this new technology are not restricted to therapeutic development, nor even to mammalian systems. We anticipate that PCR-based detection of siRNAs (such as crook siRNA) will prove a powerful adjunct for RNAi-based studies in general.

The invention claimed is:

1. A nucleic acid molecule comprising
a first part that comprises a double stranded inhibitory ribonucleic acid (RNA) molecule comprising a sense strand and an antisense strand;
and a second part that comprises a single stranded deoxyribonucleic acid (DNA) molecule, wherein the 5' end of said single stranded DNA molecule is covalently bound to the 3' end of the sense strand of the double stranded inhibitory RNA molecule, and wherein the single stranded DNA molecule comprises a nucleotide sequence that anneals to a predetermined DNA template and functions as a primer to amplify the predetermined DNA template in a polymerase chain reaction (PCR).

2. The nucleic acid molecule according to claim 1, wherein said single stranded DNA molecule comprises at least one copy of SEQ ID NO:1, wherein the 5' end of SEQ ID NO:1 is contiguous with the 3' end of the single stranded DNA molecule that functions as a primer.

3. The nucleic acid molecule according to claim 1, wherein said single stranded DNA molecule is adapted to be resistant to nuclease digestion.

4. The nucleic acid molecule according to claim 1, wherein said single stranded DNA molecule is between 10 and 40 nucleotides in length.

5. The nucleic acid molecule according to claim 1, wherein said double stranded inhibitory RNA molecule is at least 19 base pairs in length.

6. The nucleic acid molecule according to claim 1, wherein said double stranded inhibitory RNA molecule is between 18 and 29 base pairs in length.

7. The nucleic acid molecule according to claim 5, wherein said double stranded inhibitory RNA molecule is about 21 base pairs in length.

8. The nucleic acid molecule according to claim 1, wherein the sense strand of said double stranded inhibitory RNA molecule encodes at least 18 nucleotides of at least one mRNA.

9. The nucleic acid molecule according to claim 8, wherein said mRNA is encoded by a disease associated gene.

10. The nucleic acid molecule according to claim 9, wherein said disease associated gene is a viral gene.

11. The nucleic acid molecule according to claim 10, wherein said viral gene is a viral oncogene.

12. The nucleic acid molecule according to claim 10, wherein said viral gene is derived from a virus selected from the group consisting of: Human Immunodeficiency Virus, Human T Cell Leukaemia Virus, papilloma virus, papovavirus, rhinovirus, poliovirus, herpesvirus, adenovirus, Epstein Barr virus, influenza virus, hepatitis B virus and hepatitis C virus.

13. The nucleic acid molecule according to claim 12, wherein said viral gene is derived from a papilloma virus.

14. The nucleic acid molecule according to claim 12, wherein said viral gene is derived from a human papilloma virus.

15. The nucleic acid molecule according to claim 14, wherein said human papilloma virus is selected from the group consisting of: HPV-2, HPV-6, HPV-11, HPV-16, HPV-18, HPV-31, HPV-33, HPV-52, HPV-54, HPV-56, HPV-5 and HPV-8.

16. The nucleic acid molecule according to claim 15, wherein said human papilloma virus is derived from HPV-16.

17. The nucleic acid molecule according to claim 15, wherein said viral gene is E6 or E7.

18. The nucleic acid molecule according to claim 1, wherein said double stranded inhibitory RNA molecule comprises a modified base, sugar, internucleotide linkage, or combination thereof.

19. A pharmaceutical composition comprising the nucleic acid molecule according to claim 1 and a carrier.

20. An isolated cell transfected with the nucleic acid molecule according to claim 1.

21. The nucleic acid molecule according to claim 17, wherein said viral gene is E7.

22. The nucleic acid molecule according to claim 1, wherein said single stranded DNA molecule is between 15 and 30 nucleotides in length.

23. The nucleic acid molecule according to claim 1, wherein said double stranded inhibitory RNA molecule is between 21 and 27 base pairs in length.

24. The nucleic acid molecule according to claim 14, wherein said single stranded DNA molecule is between 10 and 40 nucleotides in length.

25. The nucleic acid molecule according to claim 14, wherein said single stranded DNA molecule is between 15 and 30 nucleotides in length.

26. The nucleic acid molecule according to claim 14, wherein said double stranded inhibitory RNA molecule is between 21 and 27 base pairs in length.

27. The nucleic acid molecule according to claim 14, wherein said double stranded inhibitory RNA molecule is at least 19 base pairs in length.

28. The nucleic acid molecule according to claim 14, wherein said double stranded inhibitory RNA molecule is between 18 and 29 base pairs in length.

29. The nucleic acid molecule according to claim 14, wherein said double stranded inhibitory RNA molecule is about 21 base pairs in length.

30. The nucleic acid molecule according to claim 14, wherein said double stranded inhibitory RNA molecule comprises at least 18 base pairs in length.

31. The nucleic acid molecule according to claim 21, wherein said single stranded DNA molecule comprises at least 10 nucleotides in length.

32. The nucleic acid molecule according to claim 21, wherein the nucleotide sequence comprising the sense strand inhibitory RNA and the single stranded DNA comprises SEQ ID NO:15.

33. The nucleic acid molecule according to claim 21, wherein the nucleotide sequence comprising the sense strand inhibitory RNA and the single stranded DNA consists of SEQ ID NO:15.

34. A pharmaceutical composition comprising the nucleic acid molecule according to claim 21 in an amount effective to reduce the expression of E7 mRNA and a pharmaceutically acceptable carrier.

35. The nucleic acid molecule according to claim 1, wherein the double stranded inhibitory RNA molecule is a small interfering RNA (siRNA) molecule.

36. The nucleic acid molecule according to claim 14, wherein the double stranded inhibitory RNA molecule is a small interfering RNA (siRNA) molecule.

37. A method for detecting the presence of a double stranded inhibitory RNA molecule in a sample comprising the steps of:
  i) forming a preparation comprising the nucleic acid molecule of claim 1, wherein the single stranded DNA present in the nucleic acid molecule of claim 1 is a first primer; a single stranded DNA molecule adapted to anneal to a predetermined DNA template and function as a second primer for a polymerase chain reaction (PCR); a predetermined DNA template; a thermostable DNA polymerase; and PCR components including nucleoside triphospahtes;
  ii) providing reaction conditions that allow the amplification of said predetermined DNA template by the first primer and the second primer;
  iii) and detecting the presence of a PCR-amplified product of the predetermined DNA template, wherein the presence of the PCR-amplified product of the predetermined DNA template correlates with the presence of the double stranded inhibitory RNA molecule in the sample.

* * * * *

UNITED STATES PATENT AND TRADEMARK OFFICE
CERTIFICATE OF CORRECTION

| | | |
|---|---|---|
| PATENT NO. | : 8,067,572 B2 | Page 1 of 1 |
| APPLICATION NO. | : 11/915147 | |
| DATED | : November 29, 2011 | |
| INVENTOR(S) | : Ann Josephine Milner et al. | |

It is certified that error appears in the above-identified patent and that said Letters Patent is hereby corrected as shown below:

Cover sheet, (75) Inventors, replace "Josephine Anne Milner" with --Ann Josephine Milner--.

Signed and Sealed this
Twenty-first Day of February, 2012

David J. Kappos
*Director of the United States Patent and Trademark Office*

SEQUENCE LISTING

```
<160> NUMBER OF SEQ ID NOS: 15

<210> SEQ ID NO 1
<211> LENGTH: 7
<212> TYPE: DNA
<213> ORGANISM: Artificial Sequence
<220> FEATURE:
<223> OTHER INFORMATION: Synthetic Primer

<400> SEQUENCE: 1 gcgaagc                                                                    7

<210> SEQ ID NO 2
<211> LENGTH: 35
<212> TYPE: DNA
<213> ORGANISM: Artificial Sequence
<220> FEATURE:
<223> OTHER INFORMATION: Synthetic Primer

<400> SEQUENCE: 2
tcacctcatc ccgcgaagcc catatatgga gttcc                                    35

<210> SEQ ID NO 3
<211> LENGTH: 25
<212> TYPE: DNA
<213> ORGANISM: Artificial Sequence
<220> FEATURE:
<223> OTHER INFORMATION: Synthetic Primer

<400> SEQUENCE: 3
agcgatgact aatacgtaga tgtac                                               25

<210> SEQ ID NO 4
<211> LENGTH: 25
```

```
<212> TYPE: DNA
<213> ORGANISM: Artificial Sequence
<220> FEATURE:
<223> OTHER INFORMATION: Synthetic Primer

<400> SEQUENCE: 4
cgcggatcct cacctcatcc cgcga                                              25

<210> SEQ ID NO 5
<211> LENGTH: 31
<212> TYPE: DNA
<213> ORGANISM: Artificial Sequence
<220> FEATURE:
<223> OTHER INFORMATION: Synthetic Primer

<400> SEQUENCE: 5
gcggaattca agtaggaaag tcccataagg t                                       31

<210> SEQ ID NO 6
<211> LENGTH: 20
<212> TYPE: DNA
<213> ORGANISM: Artificial Sequence
<220> FEATURE:
<223> OTHER INFORMATION: Synthetic Primer

<400> SEQUENCE: 6
gtcaataggg ggcgtacttg                                                    20

<210> SEQ ID NO 7
<211> LENGTH: 30
<212> TYPE: DNA
<213> ORGANISM: Artificial Sequence
<220> FEATURE:
<223> OTHER INFORMATION: Synthetic Primer

<400> SEQUENCE: 7
gtaatacgac tcactatagg gcgaattggg                                         30

<210> SEQ ID NO 8
<211> LENGTH: 30
<212> TYPE: DNA
<213> ORGANISM: Artificial Sequence
<220> FEATURE:
<223> OTHER INFORMATION: Synthetic Primer

<400> SEQUENCE: 8
cggaattcat gcatggagat acacctacat                                         30

<210> SEQ ID NO 9
<211> LENGTH: 31
<212> TYPE: DNA
<213> ORGANISM: Artificial Sequence
<220> FEATURE:
<223> OTHER INFORMATION: Synthetic Primer

<400> SEQUENCE: 9
cgggaagctt atggtttctg agaacagatg g                                       31

<210> SEQ ID NO 10
<211> LENGTH: 21
<212> TYPE: DNA
<213> ORGANISM: Artificial Sequence
<220> FEATURE:
<223> OTHER INFORMATION: Synthetic Primer

<400> SEQUENCE: 10
aagcagcgtg agtttgagag c                                                  21
```

```
<210> SEQ ID NO 11
<211> LENGTH: 21
<212> TYPE: DNA
<213> ORGANISM: Artificial Sequence
<220> FEATURE:
<223> OTHER INFORMATION: Synthetic Primer

<400> SEQUENCE: 11
agggtgaact ttggtgggaa c                                              21

<210> SEQ ID NO 12
<211> LENGTH: 21
<212> TYPE: DNA
<213> ORGANISM: Artificial Sequence
<220> FEATURE:
<223> OTHER INFORMATION: Synthetic Primer

<400> SEQUENCE: 12
cuuacgcuga guacuucgat t                                              21

<210> SEQ ID NO 13
<211> LENGTH: 38
<212> TYPE: DNA
<213> ORGANISM: Artificial Sequence
<220> FEATURE:
<223> OTHER INFORMATION: Synthetic Primer

<400> SEQUENCE: 13
cuuacgcuga guacuucgat cacctcatcc cgcgaagc                            38

<210> SEQ ID NO 14
<211> LENGTH: 21
<212> TYPE: DNA
<213> ORGANISM: Artificial Sequence
<220> FEATURE:
<223> OTHER INFORMATION: Synthetic Primer

<400> SEQUENCE: 14
cguacgcgga auacuucgat t                                              21

<210> SEQ ID NO 15
<211> LENGTH: 38
<212> TYPE: DNA
<213> ORGANISM: Artificial Sequence
<220> FEATURE:
<223> OTHER INFORMATION: Synthetic DNA/RNA Hybrid

<400> SEQUENCE: 15
aggaggauga aauagauggt cacctcatcc cgcgaagc                            38
```